(12) United States Patent
Nel et al.

(10) Patent No.: US 10,111,650 B2
(45) Date of Patent: Oct. 30, 2018

(54) PEDICLE MOUNTABLE RETRACTOR SYSTEM

(71) Applicant: MINIMAL INVASIVE TECHNOLOGIES (PTY) LTD., Pretoria (ZA)

(72) Inventors: Louis Jacobus Nel, Pretoria (ZA); Gert Stephanus Becker, Pretoria (ZA)

(73) Assignee: Minimal Invasive Technologies (Pty) Ltd., Pretoria (ZA)

( * ) Notice: Subject to any disclaimer, the term of this patent is extended or adjusted under 35 U.S.C. 154(b) by 0 days.

(21) Appl. No.: 15/172,589

(22) Filed: Jun. 3, 2016

(65) Prior Publication Data
US 2016/0354073 A1 Dec. 8, 2016

(30) Foreign Application Priority Data

Jun. 4, 2015 (ZA) .................................. 2015/04028
Jun. 11, 2015 (ZA) .................................. 2015/04252

(51) Int. Cl.
*A61B 17/70* (2006.01)
*A61B 17/02* (2006.01)

(52) U.S. Cl.
CPC ............ *A61B 17/025* (2013.01); *A61B 17/02* (2013.01); *A61B 17/708* (2013.01); *A61B 17/7032* (2013.01); *A61B 17/7037* (2013.01); *A61B 17/7082* (2013.01); *A61B 17/7085* (2013.01); *A61B 17/7086* (2013.01); *A61B 2017/0256* (2013.01)

(58) Field of Classification Search
CPC ........................... A61B 17/02–17/0293; A61B 17/7074–17/7092
See application file for complete search history.

(56) References Cited

U.S. PATENT DOCUMENTS

| 5,219,349 A * | 6/1993 | Krag ................. A61B 17/7077 606/105 |
| 5,728,046 A * | 3/1998 | Mayer ............... A61B 17/0293 600/210 |
| 2006/0069391 A1* | 3/2006 | Jackson ............ A61B 17/7037 606/62 |
| 2008/0077138 A1* | 3/2008 | Cohen ................. A61B 17/708 606/86 A |
| 2008/0125788 A1* | 5/2008 | Cohen ............... A61B 17/7085 606/104 |

(Continued)

FOREIGN PATENT DOCUMENTS

| EP | 2 777 573 | 9/2014 |
| EP | 2 898 836 | 7/2015 |
| WO | WO 2015/116624 | 8/2015 |

OTHER PUBLICATIONS

Extended European Search Report dated Oct. 26, 2016 in Application No. 161762999.1.

*Primary Examiner* — Jan Christopher Merene
*Assistant Examiner* — Steven Cotroneo
(74) *Attorney, Agent, or Firm* — Knobbe, Martens, Olson & Bear LLP

(57) ABSTRACT

A retractor system 100 comprises a first tower 102 which is mountable on a first surgical screw 12.1. A second tower 104 is mountable on a second surgical screw 12.2. A link 106 extends between the first and second towers. At least a first elongate retractor element 108 for at least one of muscle, tissue and nerve structures is movably mountable on the link.

10 Claims, 14 Drawing Sheets

(56) References Cited

U.S. PATENT DOCUMENTS

| | | | |
|---|---|---|---|
| 2008/0125817 A1* | 5/2008 | Arnett | A61B 17/7002 |
| | | | 606/319 |
| 2011/0166606 A1* | 7/2011 | Stihl | A61B 17/7091 |
| | | | 606/279 |
| 2012/0296171 A1 | 11/2012 | Lovell et al. | |
| 2012/0303034 A1* | 11/2012 | Woolley | A61B 17/0206 |
| | | | 606/90 |
| 2013/0310942 A1 | 11/2013 | Abdou | |
| 2014/0031874 A1* | 1/2014 | Kucharzyk | A61B 17/7076 |
| | | | 606/279 |
| 2014/0277198 A1* | 9/2014 | Stad | A61B 17/7074 |
| | | | 606/86 A |
| 2015/0051648 A1* | 2/2015 | May | A61B 17/7086 |
| | | | 606/264 |
| 2015/0066088 A1* | 3/2015 | Brinkman | A61B 17/708 |
| | | | 606/264 |
| 2015/0164569 A1* | 6/2015 | Reitblat | A61B 17/7077 |
| | | | 606/279 |
| 2016/0345952 A1* | 12/2016 | Kucharzyk | A61B 17/0206 |

* cited by examiner

PEDICLE MOUNTABLE RETRACTOR SYSTEM

BACKGROUND

Field of the Invention

This application relates to a medical device and more particularly to a retractor system for use in spinal fusion procedures.

Description of the Related Art

Spinal fusion is a surgical technique used to join two or more vertebrae. In most cases, the fusion is augmented by at least one of: placement of an anterior inter-vertebrae fusion device; and a process called fixation, involving the posterior placement of pedicle screws in pedicles of adjacent vertebrae and rods extending between the pedicle screws, to stabilize the vertebrae and facilitate bone fusion.

Access to the anterior inter-vertebral space is required in order to place the anterior inter-body fusion device. There are two ways of accessing the anterior inter-vertebral space. Firstly, it may be accessed through the abdomen, but this procedure may be too invasive. Secondly, it may be approached from posterior, past the spinal cord and the nerve roots.

In establishing access to the anterior inter-body space from posterior, damage may be caused to the spinal structures. To prevent this, a minimal invasive approach is used. However, management of the posterior soft tissue and neural structures during this minimal invasive approach makes access to the anterior inter-vertebral space more challenging. Current devices and procedures or methods provide for retractors for the soft tissue and nerve structures to be anchored to the operating table or to be held by hand by a human operating assistant. These devices and methods are unreliable and potentially dangerous, at least because they are susceptible to relative movement between the body of the patient and the anchor.

In minimal invasive surgical procedures, a tube is connected to the pedicle screw to keep control over the screw during placement in the pedicle and to facilitate insertion of the rod. Hence, the pedicle screw normally forms part of a pedicle screw and releasable tube assembly. Towards the end of the procedure, the tube is released from the screw and removed.

The optimum trajectory for placing the screws is determined by the anatomical features of the pedicles to be linked. Imaginary axial lines through the screws intersect in space. The known tubes are in excess of 100 mm in length, extend along the lines and they often interfere in space, which may lead to inaccurate placement of the pedicle screws. Furthermore, the known assemblies comprise a cumbersome, complex and time consuming mechanism for releasing the tube from the pedicle screw.

SUMMARY OF THE INVENTION

Accordingly, in some aspects of the present disclosure a retractor system is provided which provides a useful alternative to the known systems.

In some aspects a retractor system is provided comprising:
- a first tower which is mountable on a first surgical screw;
- a second tower which is mountable on a second surgical screw;
- a link extending between the first and second towers; and
- at least a first elongate retractor element for at least one of muscle, tissue and nerve structures and which at least first element is movably mountable on the link.

In this specification the term "surgical screw" is used to denote a screw which is designed, configured and intended to be driven into the body of a mammal, such as into a bone of the body and includes within its scope, but is not limited to, a pedicle screw which, in use, is driven into a pedicle of a vertebra of the mammal.

At least one of the first and second towers may comprise a screw gripping formation comprising elastic spring biased parts for removably mounting the first tower on the first surgical screw.

At least one of the first and second surgical screws may comprise a head having an outer transverse cross-sectional area and a threaded shank and the at least one of the first and second surgical screws may define an axial bore therethrough.

The head may comprise a tubular sidewall providing the outer cross-sectional area and the head may be connected to the shank in articulated manner.

The head may be connected to the shank by a ball and socket joint.

At least one of the first tower and second tower may comprise a first tube comprising or providing the screw gripping formation.

The first tube may have a distal end defining a distal opening and a proximal end defining a proximal opening and may define an axial bore extending between the distal opening and the proximal opening, the first tube, towards the distal end thereof, may comprise the screw gripping formation and may define at least first and second slots extending axially from the distal end partially towards the proximal end to form at least first and second axially extending tube parts which are spring biased towards a first configuration to grip the head by pinching the head between them, and wherein the at least first and second tube parts are manipulatable against the bias to a second configuration, to release the head.

The tubular sidewall of the head may define diametrically opposed notches extending axially form a proximal end of the head.

At least the first tower may comprise a centre shaft and an inner tube having an external diameter which is less than an inner diameter of the first tube and which are coaxially receivable in the first tube.

The centre shaft may comprise a transverse formation at a distal end thereof, the inner tube may comprise an external thread towards a distal end thereof, the centre shaft may be coaxially receivable in the bore of the first tube with the transverse formation locating in the diametrically opposed notches of the head of the screw, the inner tube may be coaxially receivable between the centre shaft and the first tube and the external thread may cooperate with a complementary internal thread in the first tube to bear onto and lock the transverse formation of the centre shaft in the diametrically opposed notches.

The link may be removably connectable to the centre shafts of the first and second towers respectively.

The link may comprise a first part which may be removably connectable to the centre shaft of the first tower to extend transversely thereto, a second part which may extend transversely to both the centre shaft of the first tower and the first part of the link and a third part which may be removably connectable to the centre shaft of the second tower to extend transversely to both the centre shaft of the second tower and the second part of the link.

The first elongate retractor element may be pivotally mountable on the second part of the link to extend in a direction towards the distal ends of the first and second towers, a second elongate retractor element may be pivotally mountable on the first part of the link to extend in a direction towards the distal ends of the first and second towers and a third elongate retractor element may be pivotally mountable on the third part of the link to extend in a direction towards the distal ends of the first and second towers.

The at least first elongate retractor element may be mountable on the link by releasable fastening means.

In other aspects, methods of facilitating posterior access to a spinal region of a body of a mammal are provided. In some embodiments the methods comprise:
- from posterior the spinal region, securing a first tower to a first vertebra;
- from posterior the spinal region, securing a second tower to a second vertebra;
- externally of the body, linking the first and second towers to one another by a link; and
- suspending from the link at least one elongate retractor element.

The methods may include securing the first and second towers to the first and second vertebra by respective pedicle screws extending into pedicles of the first and second vertebra respectively.

Still further aspects include a releasable surgical screw and tube assembly. In some embodiments the releasable surgical screw and tube assembly comprise:
- an elongate surgical screw comprising
  - a head having an outer transverse cross-sectional area; and
  - a threaded shank,
  - the screw defining an axial bore extending therethrough; and
- a tube which is releaseably engageable with the screw, the tube having a distal end defining a distal opening and a proximal end defining a proximal opening and defining an axial bore extending between the distal opening and the proximal opening; the tube, towards the distal end thereof, comprising a screw gripping formation and defining at least first and second slots extending axially from the distal end and partially towards the proximal end to form at least first and second axially extending tube parts which are spring biased towards a first configuration to grip the head by pinching the head between them in an assembled configuration of the assembly, and the at least first and second parts of the tube being manipulatable against the bias to a second configuration, to release the head.

The head may be connected to the shank in articulated manner by a ball and socket joint.

The shank, at a proximal end thereof, may be integral with the ball of the ball and socket joint and may taper radially inwardly towards a distal end thereof.

The head may comprise a tubular sidewall and may define diametrically opposed notches extending axially form a proximal end of the sidewall.

The head may comprise at least one tube engaging formation for engaging with at least one complementary formation on the tube.

The at least one tube engaging formation may comprise first and second diametrically opposed sockets extending radially inwardly from an external face of the sidewall of the head and the at least one complementary formation may comprise diametrically opposed radially inwardly extending spigots on the screw gripping formation.

In some embodiments of the tube, the first and second parts of the tube are elastically and spring biased towards the first configuration.

In a further aspect, kits are provided. In some embodiments a kit comprises an assembly as defined above and a separate tool for use in releasing the tube from the screw. The tool may be used manually to manipulate the first and second parts of the tube from the first configuration against the bias towards the second configuration, to release the head.

BRIEF DESCRIPTION OF THE DRAWINGS

The invention will now further be described, by way of example only, with reference to the accompanying diagrams wherein.

DETAILED DESCRIPTION

Figure 1:
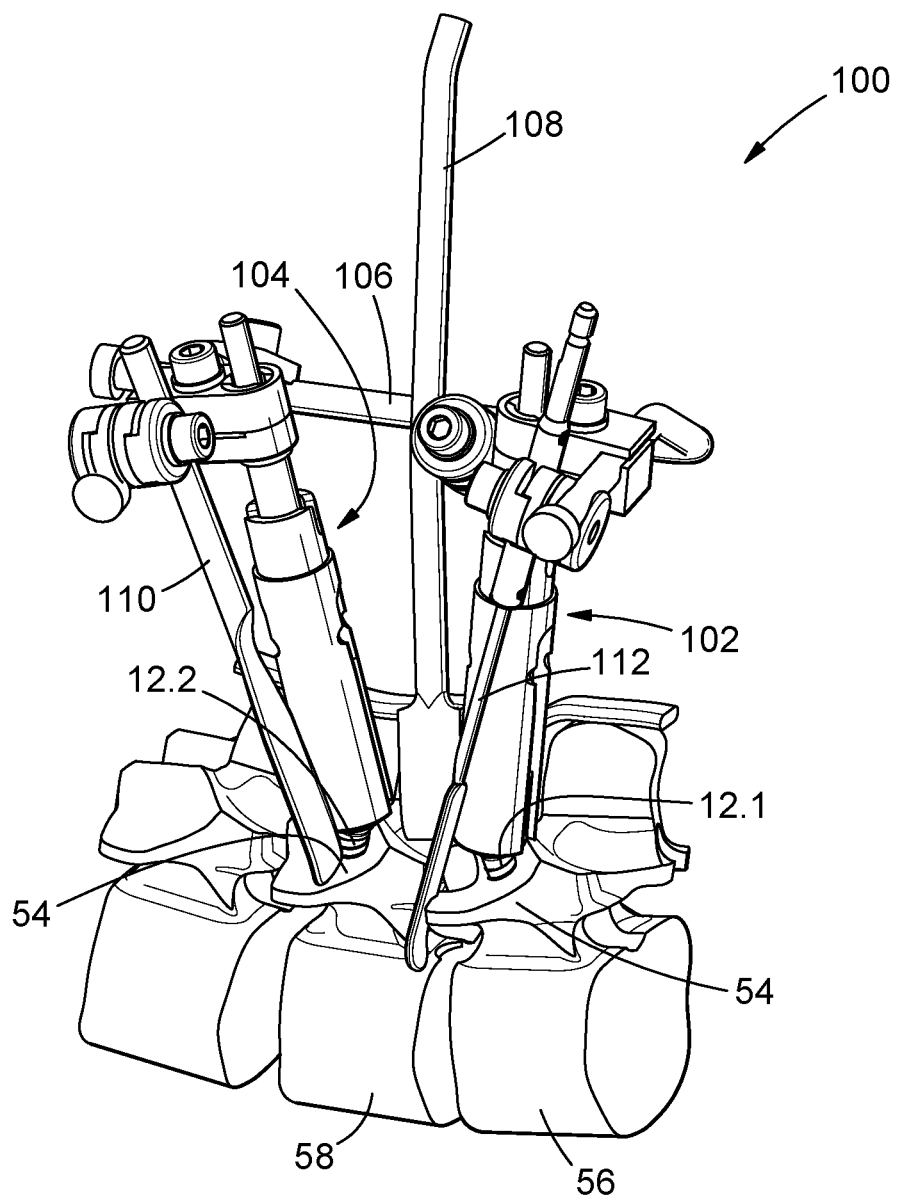
FIG. 1 is a diagrammatic perspective view of a retractor system which is mountable on first and second pedicle screws extending into pedicles of first and second vertebrae.
Figure 9:
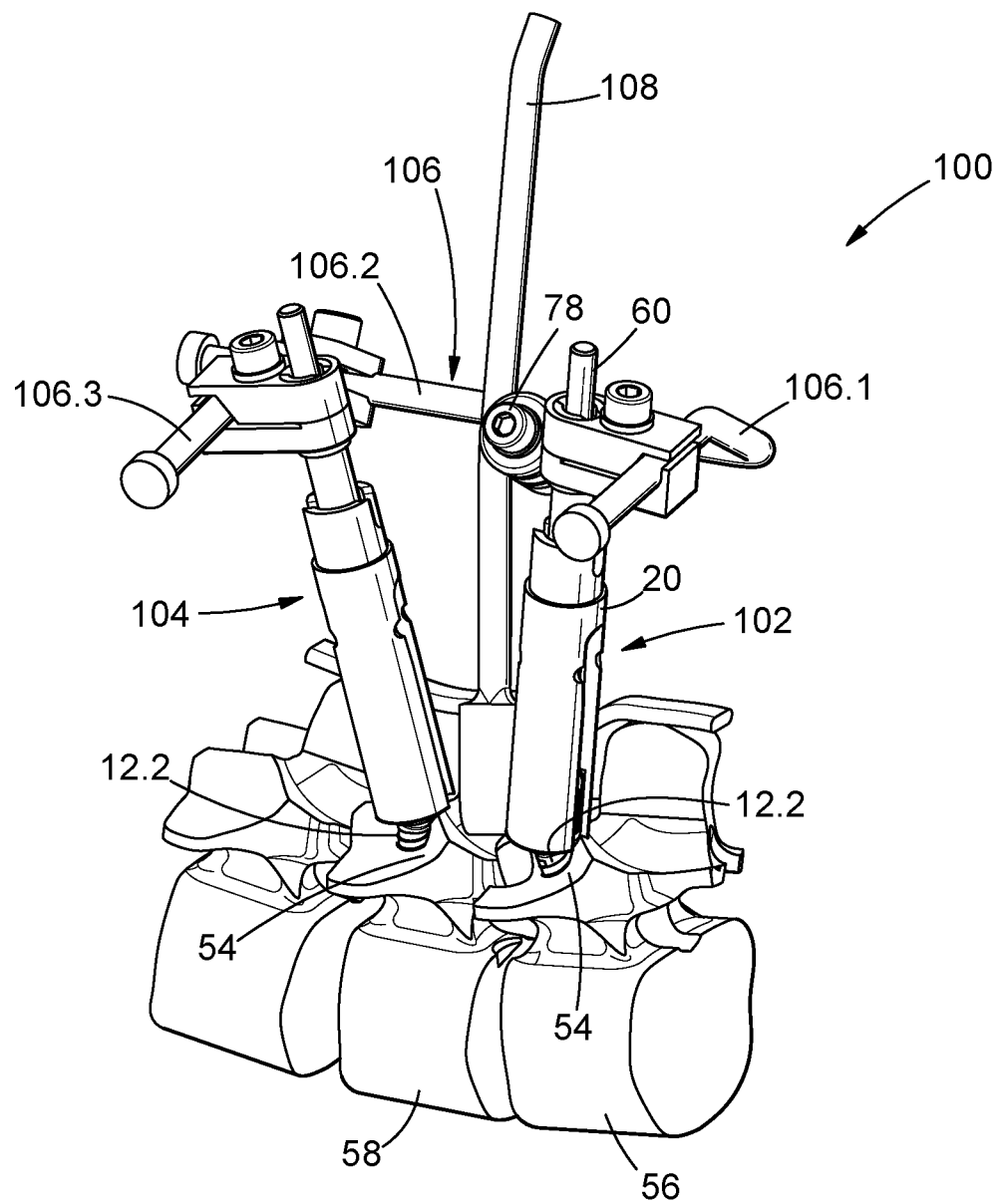
FIG. 9 is a view similar to FIG. 8, but with a first retractor element mounted on the link.
Figure 10:
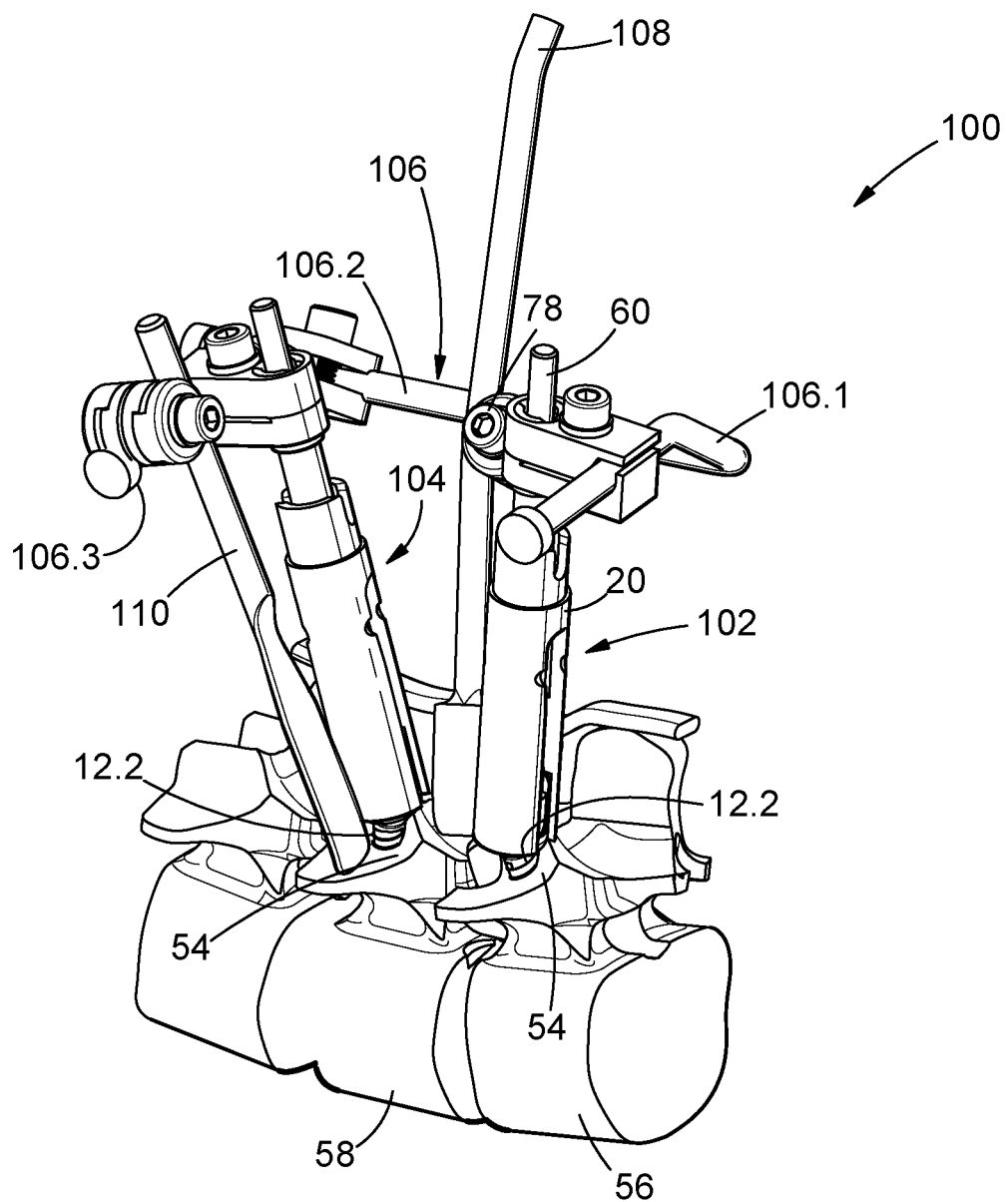
FIG. 10 is a view similar to FIG. 9, but also with a second retractor element mounted on the link.

An example embodiment of a retractor system is generally designated by the reference numeral 100 in FIGS. 1, 9 and 10.

The retractor system 100 comprises a first tower 102 which is mountable on a first surgical screw, in the example embodiment in the form of a pedicle screw 12.1. A second tower 104 is mountable on a second pedicle screw 12.2. A link 106 extends between the first and second towers and at least a first elongate retractor element 108 is mountable on the link.

In the example embodiment, the first and second pedicle screws 12.1 and 12.2 are similar in configuration and the first and second towers 102 and 104 are also similar in configuration and therefore the first pedicle screw 12.1 and first tower 102 only will be described in more detail below.

Figure 2:
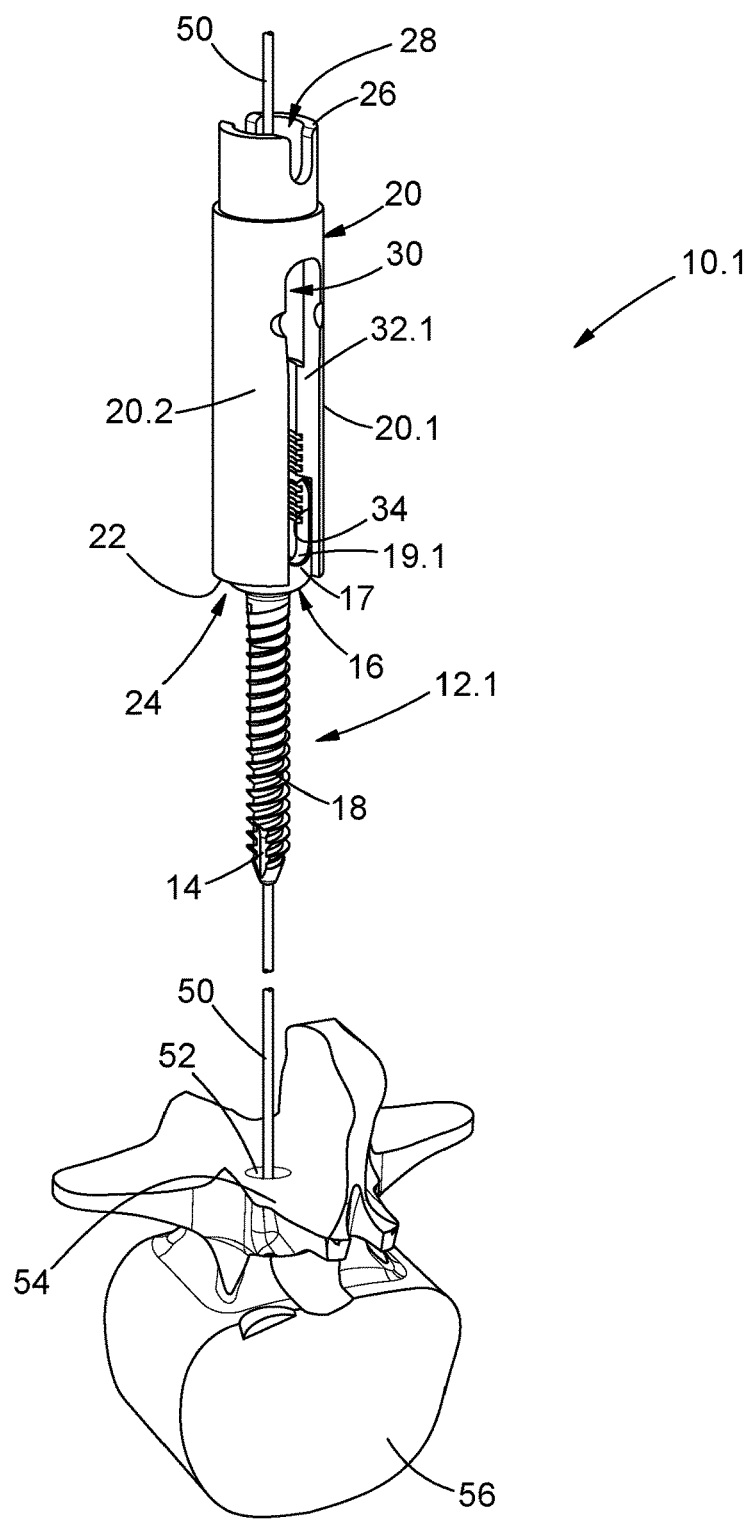
FIG. 2 is a diagrammatic perspective view illustrating placing in the pedicle, the pedicle screw, which forms part of a pedicle screw and first tube assembly.

Referring to FIG. 2, the pedicle screw 12.1 forms part of a releasable assembly 10.1 comprising the pedicle screw and a first tube 20 of the first tower 102. The pedicle screw 12.1 defines an axial bore 14 and comprises a region, for example a head 16, having an outer transverse cross-sectional area $a_1$ (shown in FIG. 14(a)) between outer faces of the head and a threaded shank 18.

Referring mainly to FIG. 2, the axial bore 14 of the screw extends through the head 16 having a tubular sidewall 17 and the shank 18. In the example embodiment, the head 16 and shank 18 are connected to one another in articulated manner by a ball and socket joint 36 (best shown in FIGS. 6, 14(a) and 14(b)). A locking ring 37 (also shown in FIGS. 6, 14(a) and 14(b), but omitted from the other figures for the sake of better clarity) is provided between the ball and socket. The locking ring 37 is movable between a first position (not shown) wherein it allows movement between the ball and socket (and hence the head and shank) and a second position (shown in FIG. 6) wherein it locks the ball and socket rigidly relative to one another. The head 16 defines diametrically opposed notches 19.1 and 19.2 (best shown in FIG. 15) extending axially from the proximal end of the tubular head.

Referring mainly to FIG. 2, the assembly 10.1 also comprises a first tube 20 of the tower 102 and which first tube has a distal end 22 defining a distal opening 24, a proximal end 26 defining a proximal opening 28 and defines a bore 30 extending between the distal opening and the proximal opening. The first tube 20, towards the distal end 22 thereof, comprises at least first and second axially extending parts 20.1 and 20.2 which are separated by at least a first axial slot 32.1 and second axial slot 32.2 (shown in FIGS. 14(a) and (b)) extending from the distal end 22 partially towards the proximate end 26, to form a releasable screw gripping formation 34 for gripping head 16 of the screw. The formation has an internal transverse cross-sectional area between inner faces of the formation. The at least first and second parts 20.1 and 20.2 are elastically spring biased towards a first configuration (shown in FIG. 14(a)) wherein the internal cross-sectional area is less than the outer cross-sectional area $a_1$ of the head 16 of the screw. The at least first and second parts are manipulatable (as will be described below) to a second configuration (shown in FIG. 14(b)) wherein the internal cross-sectional area is larger than the outer cross-sectional area $a_1$ of the head of the screw, thereby to release the screw.

Figures 14A, 14B:
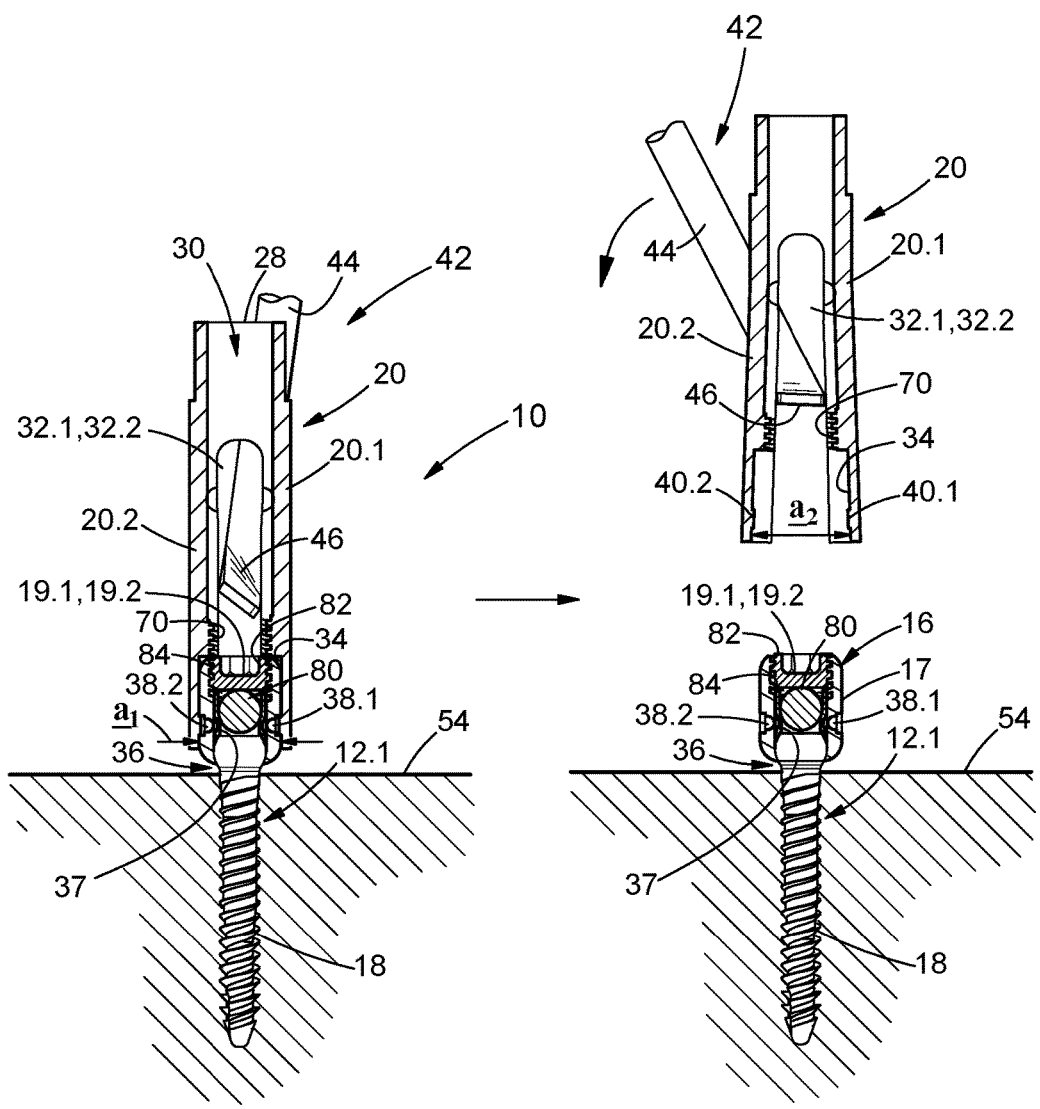
FIG. 14A and FIG. 14B are sectional views illustrating release with the tool of the first tube from the screw.
Figure 15:
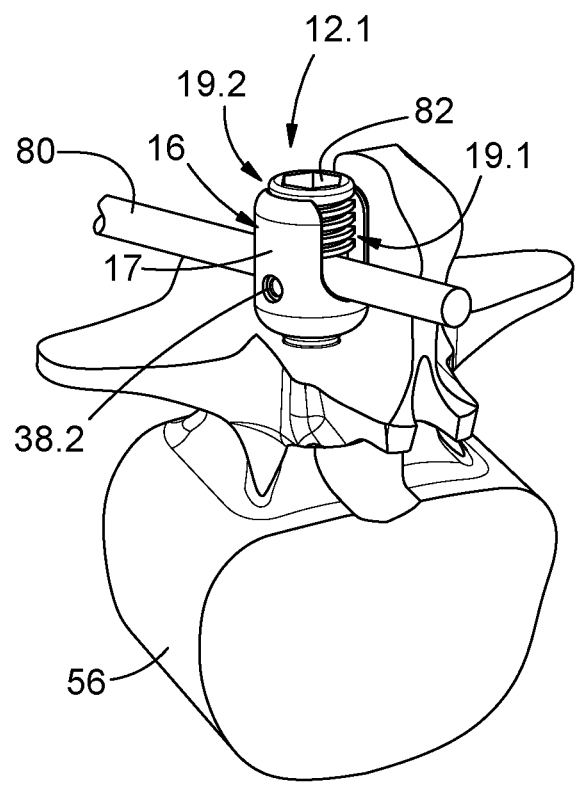
FIG. 15 is a diagrammatic perspective view with the pedicle screw in position on the pedicle and the rod secured to the pedicle screw by another screw.

Also as shown in FIGS. 14(a) and 14(b), the head 16 further defines first tube engaging formations in the form of first and second diametrically opposed transversely extending socket formations 38.1 and 38.2 for removably receiving complementary spigot formations 40.1 and 40.2 respectively, which are integrally provided on inner faces of the first and second parts 20.1, 20.2 respectively of the tube.

Figure 13:
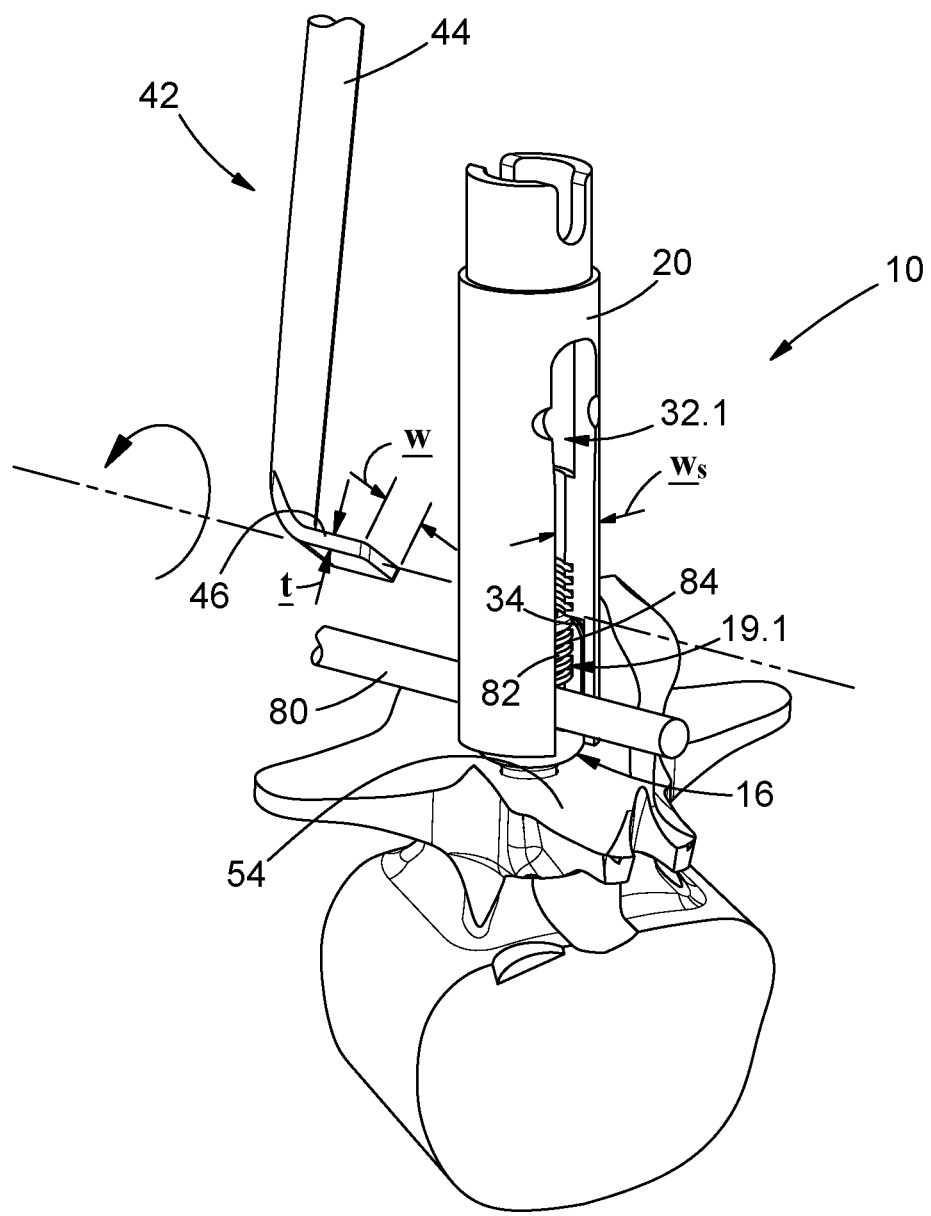
FIG. 13 is an exploded perspective view of the screw and first tube assembly and a tool for releasing the first tube from the screw.

A tool 42, which is shown in FIGS. 13, 14(a) and 14(b) is provided as part of a kit to remove the first tube 20 from the pedicle screw 12.1 as will be described below. In the example embodiment, the tool 42 is L-shaped comprising a handle 44 and an operative part 46. As shown in FIG. 13, the operative part has a thickness dimension t, which is less than the width $w_s$ of the slot 32.2 and a width dimension w, which is more than the width $w_s$ of the slot 32.2.

Referring again to FIG. 2, in use, the assembly 10.1 comprising pedicle screw 12.1 and first tube 20 is guided along a guide wire 50 extending into a pilot hole 52 in a pedicle 54 of first vertebra 56 towards the hole 52. By utilizing a special screw driver (not shown), the pedicle screw 12.1 of the assembly 10.1 is driven into the pilot hole 52 until it is firmly anchored in the hole and the assembly 10.1 stands proud of the pedicle 54 of the vertebra 56.

Figure 3:
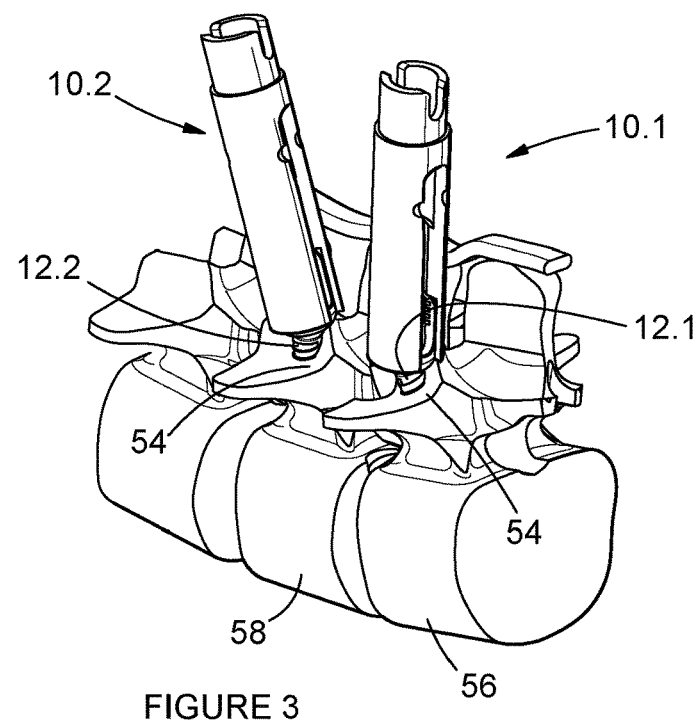
FIG. 3 is a diagrammatic perspective view of first and second pedicle screw and tube assemblies in the pedicles of the first and second vertebrae.
Figure 4:
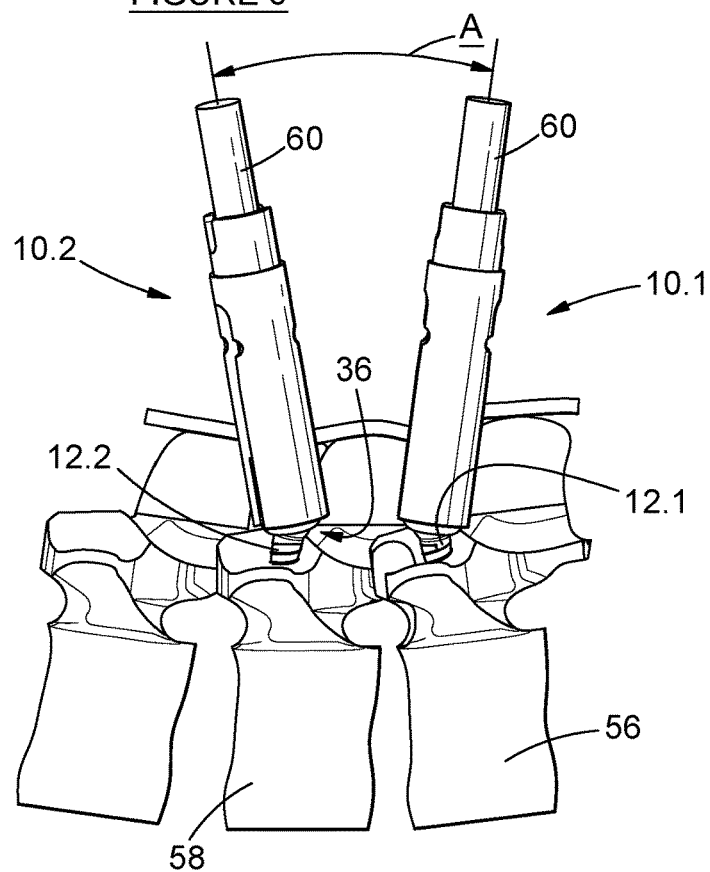
FIG. 4 is a side elevation of the pedicle screw and first tube assemblies (with respective centre shafts) in the pedicles of the first and second vertebrae.

The pedicle screw 12.2 of the second assembly 10.2 is similarly driven into a pilot hole in the pedicle 54 of vertebra 58, so that the assembly 10.2 stands proud of the pedicle 54 of vertebra 58, as shown in FIGS. 3 and 4.

Figure 5:
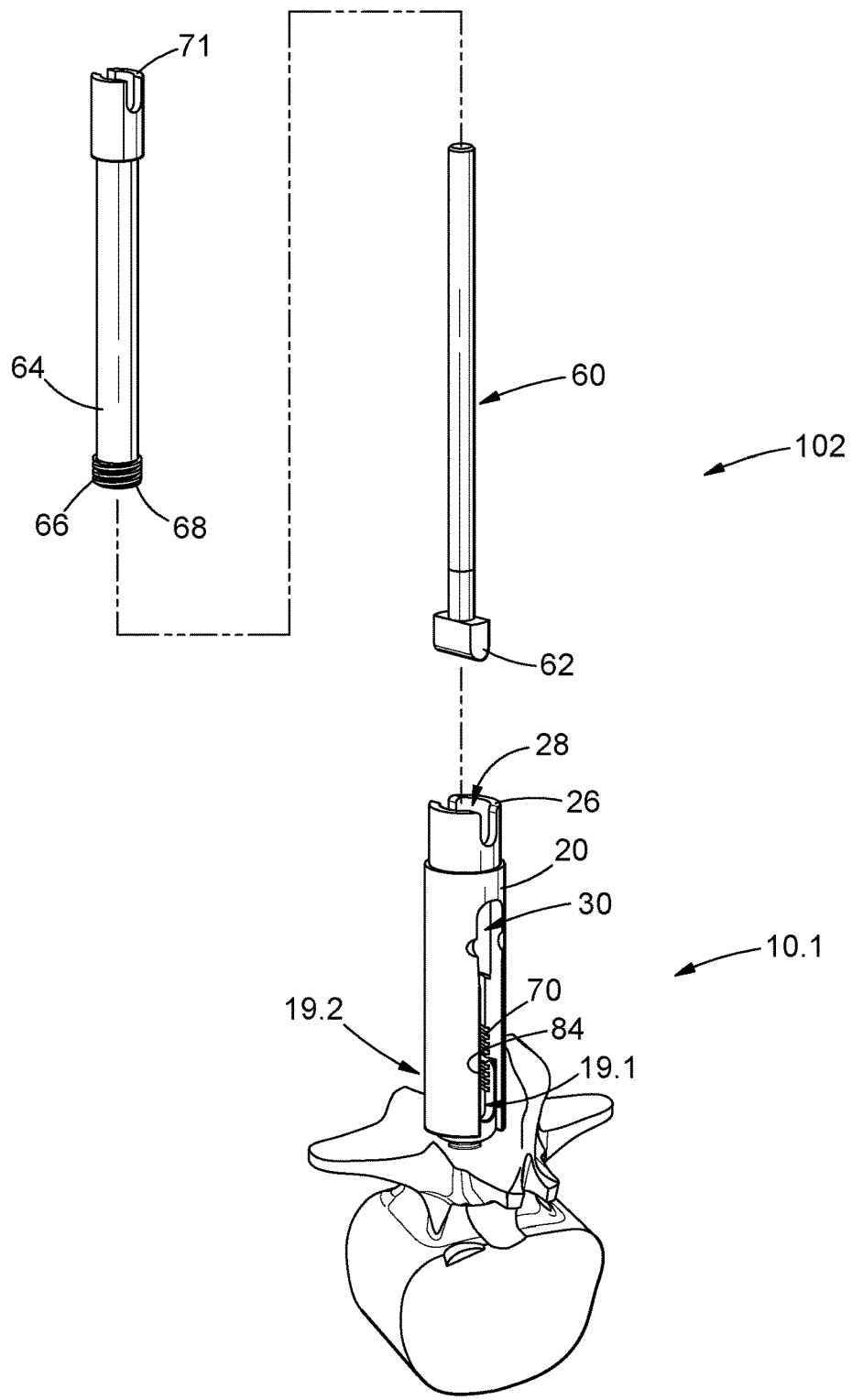
FIG. 5 is an exploded perspective view of a tower of the retractor system mounted on the first pedicle screw.

Referring to FIG. 5, the tower 102 further comprises a centre shaft 60 comprising a transverse formation 62 at a distal end thereof and an inner tube 64. The inner tube has an external diameter which is less than an internal diameter of the first tube 20. The inner tube 64 comprises an external thread 66 towards a distal end 68 thereof.

Figure 6:
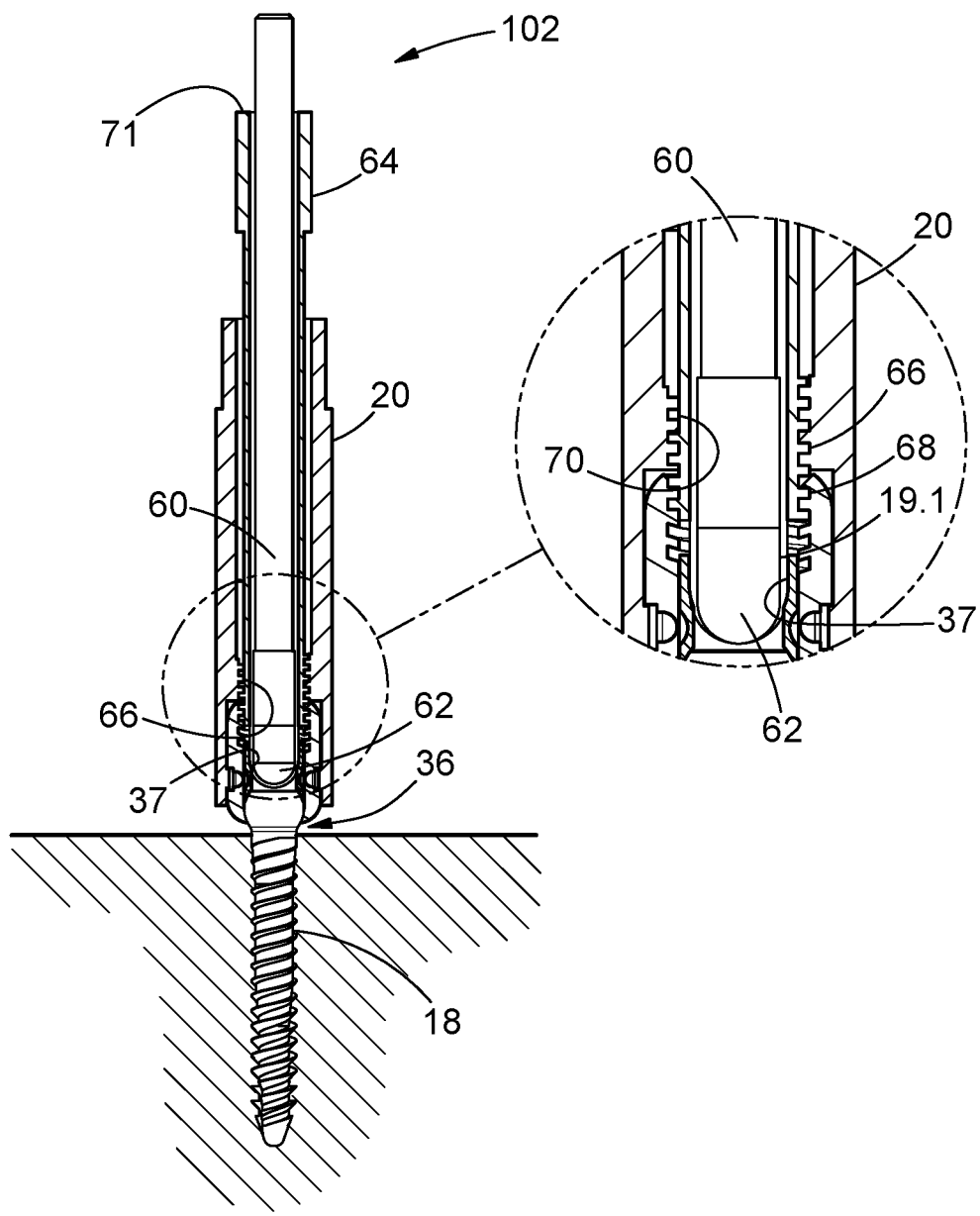
FIG. 6 is an axial section through the tower.

Referring to FIGS. 5 and 6, in use and to form the tower 102, the centre shaft 60 is mounted coaxially in the first tube 20 with the transverse formation 62 located in the diametrically opposed notches 19.1 and 19.2 in the head 16 of the screw 12.1. Due to the articulated coupling between the head of the screw and the shank, the assemblies 10.1 and 10.2 may be adjusted relative to one another, for example to diverge away from one another towards their respective proximal ends, as shown at A in FIG. 4.

Figure 7:
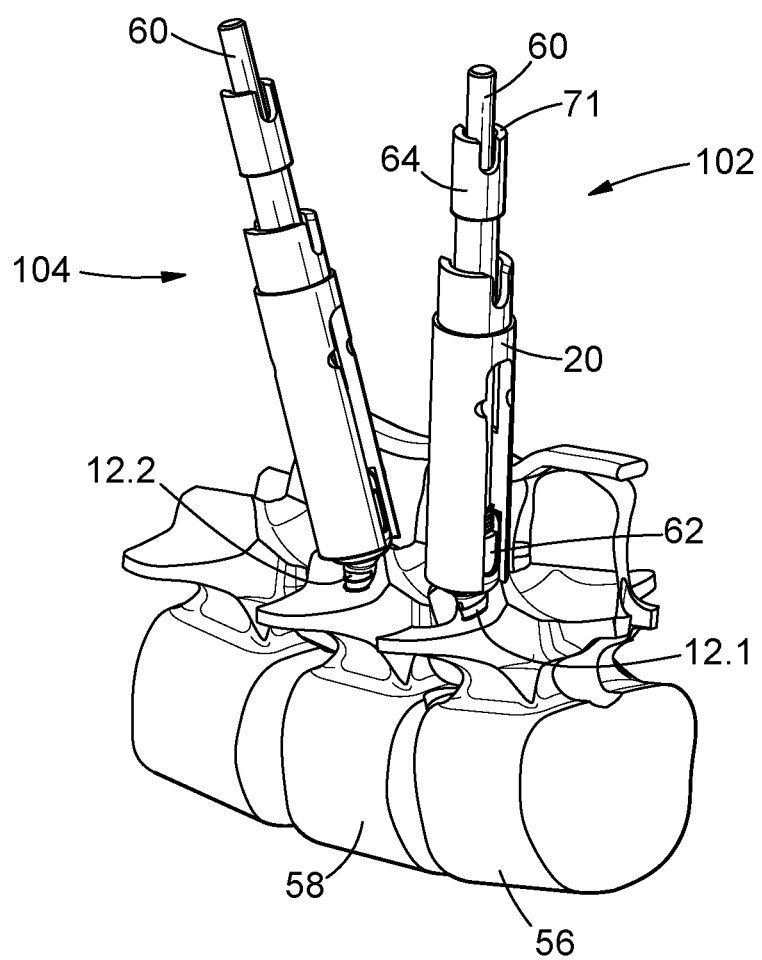
FIG. 7 is a diagrammatic perspective view of the first and second towers of the system.

The inner tube 64 is also coaxially mounted in the first tube 20 with the external thread 66 of the inner tube 64 cooperating with an internal thread 70 of the first tube 20, thereby to arrest the centre shaft 60 in the first tube 20 with the distal end 68 of the inner tube 64 bearing on the transverse formation 62 and the centre shaft 60 extending beyond the proximal end 71 of the inner tube 64. The transverse formation 62 moves the locking ring 37 to its second position, so that the head and shank are rigidly locked to one another in a selected orientation relative to one another. The second tower 104 is similarly formed. The towers 102 and 104 mounted on the respective pedicle screws 12.1 and 12.2 are shown in FIG. 7.

Figure 8:
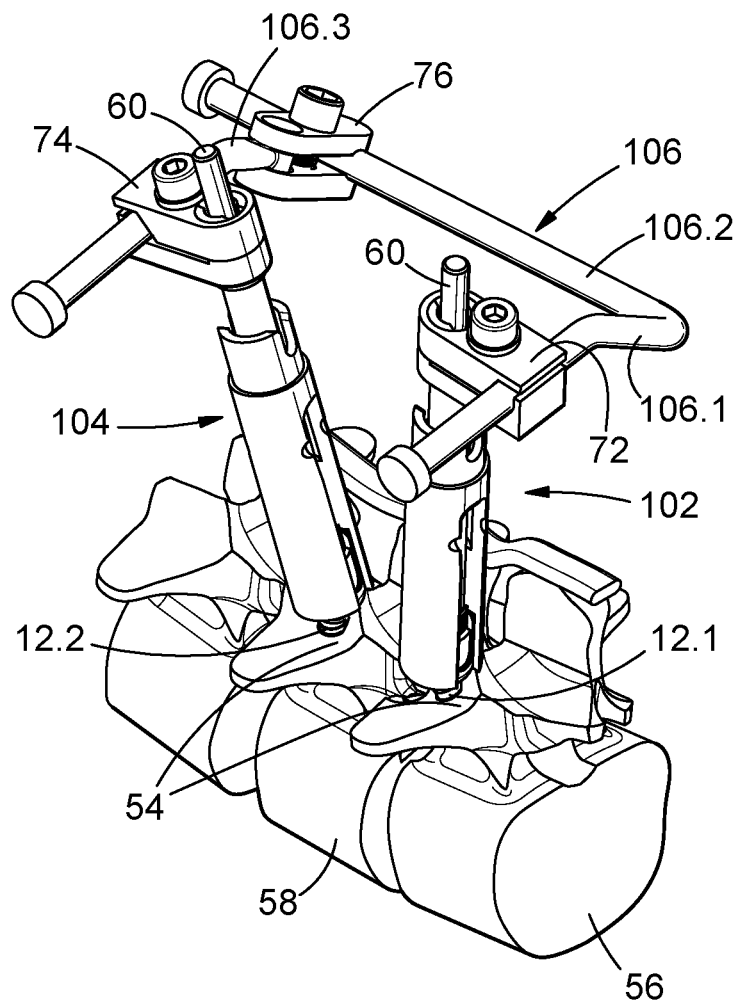
FIG. 8 is a view similar to FIG. 7, but with a link mounted between the towers.

The link 106 extending between the first and second towers is best illustrated in FIG. 8. The link 106 is secured towards the respective proximal ends of the centre shafts 60 of the first and second towers respectively. The link is secured to the centre shaft 60 of the first tower 102 by any suitable releasable fastening means 72. The link is secured to the centre shaft 60 of the second tower 104 by any suitable releasable fastening means 74. In one example embodiment, the link 106 may comprise a first part 106.1 which is releaseably secured to the centre shaft 60 of the first tower 102 to extend transversely to the centre shaft 60 of the first tower 102. The link may comprise a second part 106.2 which extends transversely to both the centre shaft 60 and the first part 106.1. The first and second parts may be formed integrally with one another. The link may comprise a third part 106.3 which is releaseably secured to the second part 106.2 by suitable releasable fastening means 76 and to the centre shaft 60 of the second tower 104 by releasable fastening means 74. The third part 106.3 extends transversely to the centre shaft 60 of the second tower 104 and to the second part 106.2.

In the example embodiment shown in FIG. 9, the at least first elongate retractor element 108 is secured to the link 106, more particularly the second part 106.2 of the link, between the first and second towers by releasable fastening means 78. The elongate retractor element 108 is rotatable or pivotable relative to the second part 106.2 of the link and also movable axially along the second part. The retractor element may be of known substantially paddle shape or configuration. The retractor element 108 is suspended from the link, extends downwardly in a direction towards the distal ends of the spaced towers 102 and 104 and may be used to manipulate and manage muscles for example, to facilitate access from posterior to the anterior inter-vertebra space.

As best shown in FIG. 10, a second retractor element 110 may similarly be mounted on the third part 106.3 of the link. The second retractor element 110 also has a known shape, extends downwardly in a direction towards the distal ends of the spaced towers 102 and 104 and may be used to manipulate and manage soft tissue for example, to facilitate access to the anterior inter-vertebra space.

As shown in FIG. 1, a third retractor element 112 may similarly be mounted on the first part 106.1 of the link. The third retractor element 112 also extends downwardly in a direction towards the distal ends of the spaced towers 102 and 104 and may be used to manipulate and manage nerve structures for example, to facilitate access to the anterior inter-vertebra space.

The retractor system 100 facilitates the placement from posterior in the anterior inter-vertebrae space (not shown) of the anterior inter-vertebrae fusion device (also not shown) through a passage way (also not shown) which is manipulatable and manageable by the above retractor elements as explained above.

Figure 11:
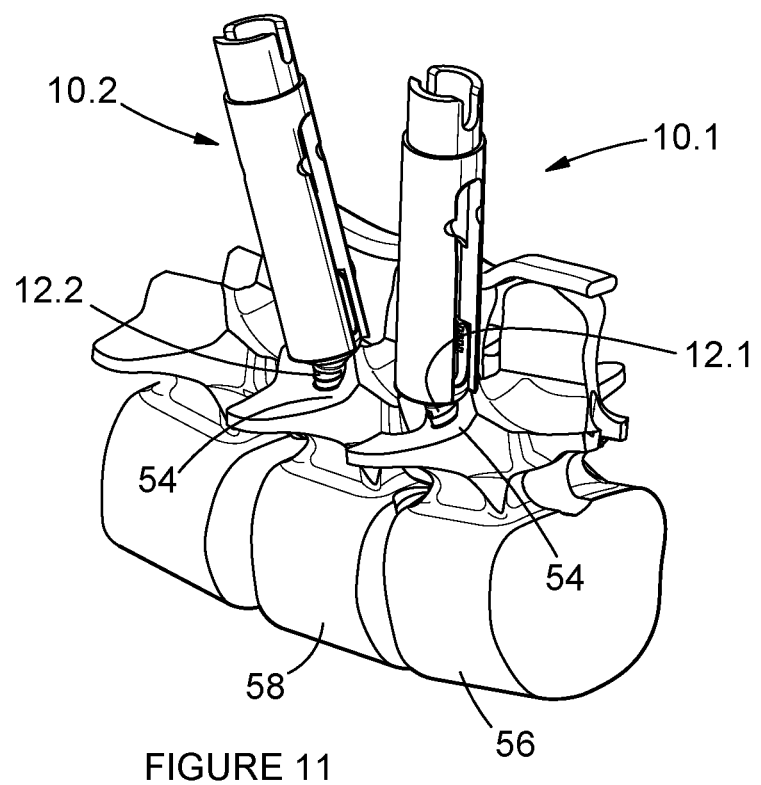
FIG. 11 is a diagrammatic perspective view of the system partially dismantled, so that only the first and second screw and tube assemblies remain.

With the anterior fusion device in position, the retractor system 100 is partially dismantled by the removal of the link 106 with retractor elements, the inner tubes 64 and the centre shafts 60. What remains are the assemblies 10.1 and 10.2 on the first and second vertebrae 56 and 58, as shown in FIG. 11. With the centre shaft 60 and inner tube 64 removed, the locking ring 37 in the assemblies 10.1 and 10.2 is released and the shank 18 and head 16 with first tube 20 are again movable relative to one another.

Figure 12:
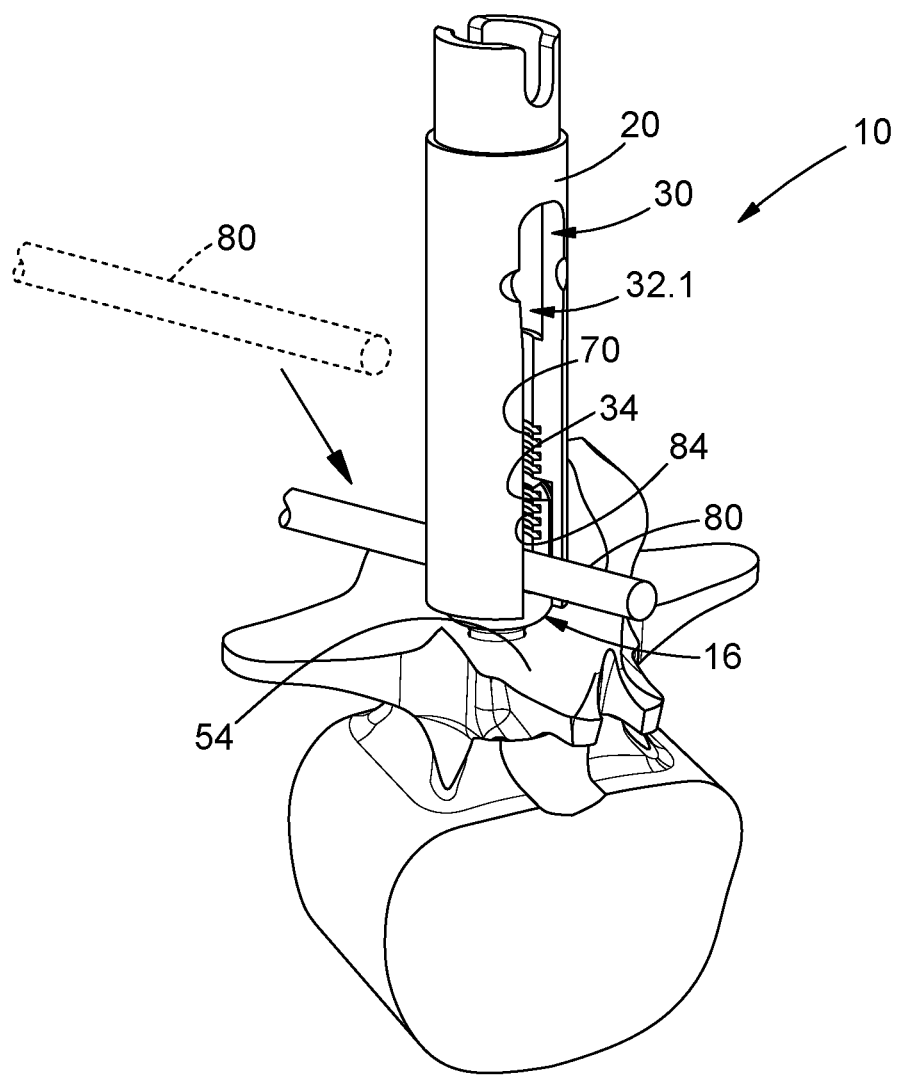
FIG. 12 is a diagrammatic perspective view of a fixation rod which is mounted on the first pedicle screw.

Referring to both FIGS. 11 and 12, towards the end of the fixation procedure, a fixation rod 80 is inserted from posterior to extend between adjacent pedicle screws 12.1 and 12.2 on adjacent vertebrae 56 and 58. As shown in FIG. 12, the rod is inserted via the slots 32.1 and 32.2 in the first tube 20 into the diametrically opposed notches 19.1 and 19.2 of the head 16 of the screw 12.1 in vertebra 56.

The rod 80 is secured to the pedicle screw 12.1 with an externally threaded other screw 82 (shown in FIG. 15), which is passed through the distal opening 28 (shown in FIG. 14(a)) and bore 30 of the first tube 20 and which cooperates with an internal thread 84 on the sidewall 17 of the screw head 16 and which thread is in phase with the internal thread 70 of the first tube 20, so that the other screw 82 can be driven continuously along first the internal thread 70 and then the internal thread 84. The rod is similarly secured to the pedicle screw 12.2 in the vertebra 58. The rod so fixed, also moves the locking ring 37 to the second position, so that head 16 and shank 18 are rigidly locked to one another.

Referring to FIGS. 14(a) and 14(b), to release the releasable first tube 20 from the screw 12.1 anchored in the pedicle 54, the operative part 46 of the tool is threaded through diametrically opposed slots 32.1 and 32.2 as shown in FIG. 14(a) and rotated until the width dimension w of the operative part extends perpendicularly between the first and second parts 20.1 and 20.2 of the first tube 20, as shown in FIG. 14(b). In this position, the internal cross-sectional area $a_2$ of the gripping formation 34 is larger than the outer cross-sectional area $a_1$ of the head 16 and the head is released. The first tube 20 is removed from the screw 12.1. The first tube on the pedicle screw 12.2 is similarly removed. The screws 12.1 and 12.2 with the fixation rod 80 extending between them remain anchored in the vertebrae 56 and 58, respectively.

The parts of the surgical screw, the tower and the link may be made of titanium or any other suitable material.

In the example embodiment, the tube 20 is pre-formed and the material selected to have a modulus of elasticity such that the first and second parts 20.1 and 20.2 are spring biased towards a resting configuration relative to one another, but are manipulatable against the bias and away from one another through a range of loaded configurations relative to one another enabling a user to mount the gripping formation 34 onto the head 16 of the screw 12.1 by moving the first and second parts 20.1 and 20.2 at least partially over the head 16 and releasing them so that the parts, still loaded, pinch the head between them.

What is claimed is:

1. A retractor system comprising:
    a first tower comprising
        a first tube having a screw gripping formation in the form of elastic spring biased parts, for removably mounting the first tower on a first surgical screw;
        a centre shaft comprising a transverse formation at a distal end thereof; and
        an inner tube having an external thread towards a distal end thereof, and having an external diameter which is less than an inner diameter of the first tube, the inner tube being coaxially receivable in the first tube,
    wherein the centre shaft is coaxially receivable in a bore of the first tube with the transverse formation locating in diametrically opposed notches of a head of the screw and wherein the inner tube is coaxially receivable between the centre shaft and the first tube and the external thread cooperates with a complementary internal thread in the first tube to bear onto and lock the transverse formation of the centre shaft in the diametrically opposed notches,
    a second tower which is mountable on a second surgical screw;
    a link extending between the first and second towers; and
    at least a first elongate retractor element for at least one of muscle, tissue and nerve structures and which at least first elongate retractor element is movably mountable on the link.

2. The retractor system as claimed in claim 1 wherein at least one of the first and second surgical screws comprises a head having an outer transverse cross-sectional area and a threaded shank and wherein the at least one of the first and second surgical screws defines an axial bore therethrough.

3. The retractor system as claimed in claim 2 wherein the head comprises a tubular sidewall providing the outer cross-sectional area and wherein the head is connected to the shank in articulated manner.

4. The retractor system as claimed in claim 3 wherein the head is connected to the shank by a ball and socket joint.

5. The retractor system as claimed in claim 3 wherein the tubular sidewall of the head defines the diametrically opposed notches extending axially form a proximal end of the head.

6. The retractor system as claimed in claim 1 wherein the link is removably connectable to the centre shaft of the first tower, and to the second tower.

7. The retractor system as claimed in claim 6 wherein the link comprises a first part which is removably connectable to the centre shaft of the first tower to extend transversely thereto, a second part which extends transversely to both the centre shaft of the first tower and the first part of the link and a third part which is removably connectable to the second tower to extend transversely to both the second tower and the second part of the link.

8. The retractor system as claimed in claim 7 wherein the first elongate retractor element is pivotally mountable on the second part of the link to extend in a direction towards the distal end of the first tower, wherein a second elongate retractor element is pivotally mountable on the first part of the link to extend in a direction towards the distal end of the first tower and wherein a third elongate retractor element is pivotally mountable on the third part of the link to extend in a direction towards the distal end of the first tower.

9. The retractor system as claimed in claim 1 wherein the at least first elongate retractor element is connected to the link by releasable fastening means.

10. The retractor system as claimed in claim 1 wherein the first tube has a distal end defining a distal opening and a proximal end defining a proximal opening and defines the bore of the first tube extending between the distal opening and the proximal opening, wherein the first tube, towards the distal end thereof, comprises the screw gripping formation and defines at least first and second slots extending axially from the distal end partially towards the proximal end to form at least first and second axially extending tube parts which are spring biased towards one another to a first configuration to grip the head by pinching the head between them, and wherein the at least first and second tube parts are manipulatable away from one another against the bias to a second configuration, to release the head.

* * * * *